United States Patent
Maenpaa et al.

(10) Patent No.: US 11,579,129 B2
(45) Date of Patent: Feb. 14, 2023

(54) METHOD AND SYSTEM FOR TESTING AND CALIBRATING GAS SENSORS

(71) Applicant: Accutron Instruments Inc., Sudbury (CA)

(72) Inventors: Douglas Maenpaa, Sudbury (CA); Steve Goulet, Sudbury (CA); Allan Irvine, Sudbury (CA); Richard Edouard Dignard, Sudbury (CA)

(73) Assignee: Accutron Instruments Inc., Sudbury (CA)

( * ) Notice: Subject to any disclaimer, the term of this patent is extended or adjusted under 35 U.S.C. 154(b) by 167 days.

(21) Appl. No.: 17/105,745

(22) Filed: Nov. 27, 2020

(65) Prior Publication Data

US 2021/0156833 A1  May 27, 2021

(30) Foreign Application Priority Data

Nov. 27, 2019 (CA) .................................. 3063026

(51) Int. Cl.
*G01N 33/00* (2006.01)
(52) U.S. Cl.
CPC ..... *G01N 33/0006* (2013.01); *G01N 33/0073* (2013.01)
(58) Field of Classification Search
CPC ................. G01N 33/0006; G01N 33/0073
See application file for complete search history.

(56) References Cited

U.S. PATENT DOCUMENTS

| | | | |
|---|---|---|---|
| 4,384,925 A * | 5/1983 | Stetter | G01N 33/0006 205/785.5 |
| 4,498,496 A * | 2/1985 | Barcellona | B01F 35/833 73/1.05 |
| 5,239,492 A * | 8/1993 | Hartwig | G01N 33/0006 73/1.07 |
| 5,405,512 A | 4/1995 | Parker | |
| 5,804,695 A * | 9/1998 | Dageforde | G01N 33/0031 73/1.07 |
| 7,401,493 B2 | 7/2008 | Forrest | |
| 9,970,755 B2 | 5/2018 | Maenpaa et al. | |
| 10,041,967 B2 | 8/2018 | Maenpaa et al. | |
| 10,177,777 B2 | 1/2019 | Dong et al. | |

(Continued)

FOREIGN PATENT DOCUMENTS

EP        1070956 A1 *  1/2001  ........... G01N 21/274

*Primary Examiner* — Herbert K Roberts
*Assistant Examiner* — Anthony W Megna Fuentes (57) ABSTRACT

A system including one or more gas sensor assemblies having one or more gas sensors. The gas sensor is for sensing a preselected gas. The gas sensor assembly includes a housing with a cavity therein, and the sensor is mounted on the housing so that the sensor is able to detect the preselected gas in the cavity. The gas sensor assembly includes a sensor control module in communication with the gas sensor, and also in communication with a central controller. Via the central controller, the sensor may be tested using a purge gas, and the sensor may be zeroed if necessary. Also, via the central controller, the sensor may be calibrated using a calibration gas mixture having the preselected gas in a known concentration. The central controller is configured for manual or automatic testing and calibration. Accordingly, the testing and calibration, whether manual or automatic, is done remotely.

4 Claims, 8 Drawing Sheets

(56) References Cited

U.S. PATENT DOCUMENTS

| | | |
|---|---|---|
| 2003/0000281 A1 | 1/2003 | Ketler et al. |
| 2014/0349408 A1* | 11/2014 | Skourlis ............. G01N 33/0006 422/83 |
| 2018/0182603 A1* | 6/2018 | Schmidt ............... G01N 27/622 |
| 2018/0259479 A1* | 9/2018 | Yoshikawa ........ G01N 27/4163 |
| 2019/0257803 A1* | 8/2019 | Brown ................. G01N 27/123 |

* cited by examiner

Time 24:15
Date Mon Oct 14, 2019

Sensor

| Tag: | 1400 level |
|---|---|
| Type: | CO 100ppm |
| S/N: | 1521 |

[ ] Sensor IP Address  [ ] Connect  [ ] Diconnect

Status: Connected!

Possible message options
Connected!
Disconnected!

Purge gas pressure  600 psi
Cal gas pressure    600 psi

Manual Controls

| ON OFF | ON OFF | [ ] | [ ] | [ ] | [ ] |
|---|---|---|---|---|---|
| Purge Pump | Cal-Gas Pump | Enter Calibrate / Test | Exit to Run | Save Zero | Save Span |

Action: Span Saved!

Sensor Response: 102 ppm
Mass Flow: 0.42 liters/min

Possible message options
Purge Pump On
Span Saved!
Zero Saved!
Exit to Run
Calibrate mode Entered!
Purge Pump Off
Cal Gas Pump Off

Session recording Controls

[ ] Start Recording   [ ] Stop Recording   [ ] Clear   [ ] Save

Status: Recording

METHOD AND SYSTEM FOR TESTING AND CALIBRATING GAS SENSORS

FIELD OF THE INVENTION

The present invention is a method and a system for testing and calibrating gas sensors.

BACKGROUND OF THE INVENTION

Gas sensors are used in many industries, especially for sensing toxic gases in the underground mining industry. Both good practice and regulations require periodic calibration testing, also known as "bump testing", to ensure that a gas sensor is working properly. Typically, in order to test a gas sensor, a technician attends at the gas sensor, and connects testing apparatus to the gas sensor. The technician may make such adjustments to the gas sensor as appear to be necessary, while the technician is at the gas sensor.

However, depending on the industry, there may be hundreds of gas sensors deployed in a facility. Accordingly, periodically bump-testing/recalibrating (e.g., once every 30 days) places a large burden on the technical staff.

In addition, in many industries, it is important that gas sensors not only be accurate, but capable of non-stop performance. In the prior art, it is intended to address this requirement by testing the gas sensors frequently, but this is insufficient, e.g., if a sensor fails between the frequently administered tests.

SUMMARY OF THE INVENTION

For the foregoing reasons, there is a need for a method and a system of testing and calibrating gas sensors that overcomes or mitigates one or more of the defects or disadvantages of the prior art.

In its broad aspect, the invention provides a system for testing and calibrating gas sensors. The system includes one or more gas sensor assemblies including one or more gas sensors. The gas sensor is for sensing a preselected gas. The gas sensor assembly includes a housing with a cavity therein, and the sensor is mounted on the housing so that the sensor is able to detect the preselected gas in the cavity. The gas sensor assembly includes a sensor control module in communication with the gas sensor, and also in communication with a central controller. Via the central controller, the sensor may be tested using a purge gas, and the sensor may be zeroed if necessary. Also, via the central controller, the sensor may be calibrated using a calibration gas mixture having the preselected gas in a known concentration. The central controller is configured for manual or automatic testing and calibration. Accordingly, the testing and calibration, whether manual or automatic, is done remotely.

In the method of the invention, to test the sensor, via the central controller, the purge gas is allowed to flow into the cavity, and once the purge gas in the cavity is equilibriated, the sensor is checked to determine whether the sensor detects zero preselected gas in the cavity. If the sensor's accuracy is acceptable, then the sensor is not adjusted. If the sensor's accuracy is not acceptable, then the sensor is zeroed. The testing, and any adjustment of the sensor, is done remotely.

Similarly, the method of the invention provides for remotely activating the flow of the calibration gas mixture into the cavity, until the calibration gas mixture is equilibriated. At that time, the sensor is checked to determine whether the sensor detects the known concentration of the preselected gas in the cavity, with acceptable accuracy. If it does, then the sensor is not adjusted. If it does not, then the sensor is adjusted, so that it reads the concentration of the preselected gas in the cavity as the known concentration. The testing, and any adjustment of the sensor, is done remotely.

BRIEF DESCRIPTION OF THE DRAWINGS

The invention will be better understood with reference to the attached drawings, in which.

DETAILED DESCRIPTION

In the attached drawings, like reference numerals designate corresponding elements throughout. Reference is made to FIGS. 1A-7 to describe an embodiment of a system 20 in accordance with the invention indicated generally by the numeral 20.

Figure 6:
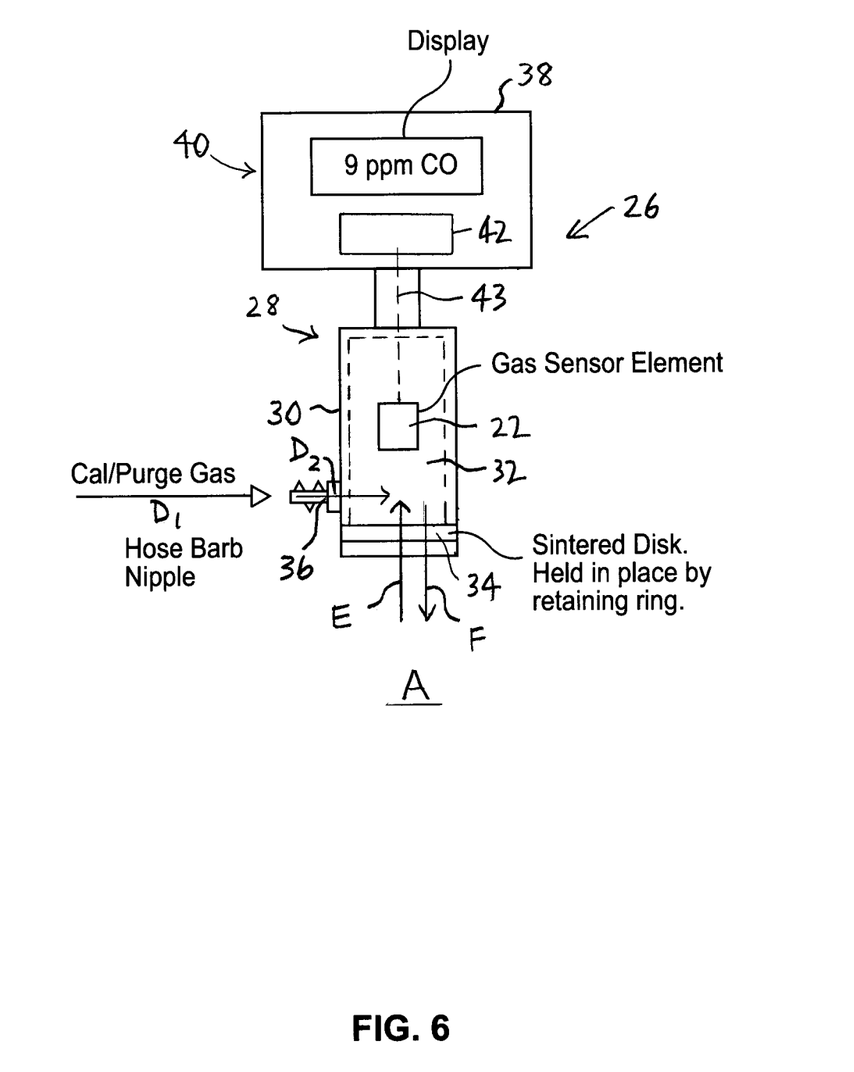
FIG. 6 is a schematic diagram of an embodiment of a gas sensor assembly of the invention.

The system 20 is for testing and calibrating one or more gas sensors 22 (FIG. 6). In one embodiment, the system 20 preferably includes a central controller 24 and a gas sensor assembly 26 (FIG. 6). As will be described, the central controller 24 preferably is connected to a communications network (not shown) via which the central controller 24 may receive signals (instructions or information), and also via which the central controller 24 may transmit signals (instructions or information). Preferably, and as can be seen in FIG. 6, the gas sensor assembly 26 includes a housing subassembly 28. The housing subassembly 28 preferably includes a housing body 30 defining a cavity 32 therein in fluid communication with an ambient atmosphere "A" (FIG. 6).

It is also preferred that the housing subassembly 28 includes a filter 34 between the cavity 32 and the ambient atmosphere "A". The filter 34 is formed to permit fluid communication therethrough, between the ambient atmosphere and the cavity 32. The housing subassembly 28 preferably also includes a fitting 36 though which a gas (not shown) is flowable into the cavity 32, as will be described.

The gas sensor assembly 26 preferably also includes the one or more sensors 22, which are in fluid communication with the cavity 32. The sensor 22 is configured to detect an amount of one or more preselected gases that are located in the cavity 32, as will also be described. The sensor 22 is configured to generate sensor data that includes the amount of the preselected gas or gases that is detected by the sensor 22.

It is also preferred that the gas sensor assembly 26 includes a sensor control module 40 (FIG. 6). The sensor control module 40 preferably includes a sensor unit processor 42, for receiving incoming signals from the central controller 24, and for transmitting outgoing signals to the central controller 24. Preferably, the sensor unit processor 42 is also configured to receive the sensor data from the sensor 22 and to transmit the sensor data in the outgoing signals to the central controller 24.

In one embodiment, the system 20 preferably also includes a test assembly 44. Preferably, the test assembly 44 includes a source 46 of a purge gas (not shown), and purge gas piping 48, for directing the purge gas from the source 46 of the purge gas to the cavity 32 of the housing body 30 via the fitting 36, as will be described. The test assembly 44 preferably also includes a purge gas flow controller 50, for allowing the purge gas to flow along the purge gas piping 48 from the source of the purge gas to the cavity at a predetermined purge gas flow rate, and for preventing the purge gas from flowing along the purge gas piping 48.

Preferably, the central controller 24 is configured to activate the purge gas flow controller 50, to cause the purge gas to flow through the purge gas piping 48 to the cavity 32, and to de-activate the purge gas flow controller 50, to prevent the purge gas from flowing through the purge gas piping 48. Upon the purge gas flow controller 50 being activated, the purge gas flow controller 50 allows the purge gas to flow into the cavity 32 at the predetermined purge gas flow rate, and the sensor 22 detects decreasing amounts of the preselected gas in the cavity 32. The sensor 22 thereupon generates the sensor data that preferably is transmitted to the central controller 24 at predetermined intervals.

The predetermined intervals at which the sensor data is transmitted to the central controller 24 may be any suitable intervals. For example, the predetermined intervals may be approximately 0.50 seconds, i.e., the sensor data may be transmitted once every 0.50 seconds.

Figure 1A:
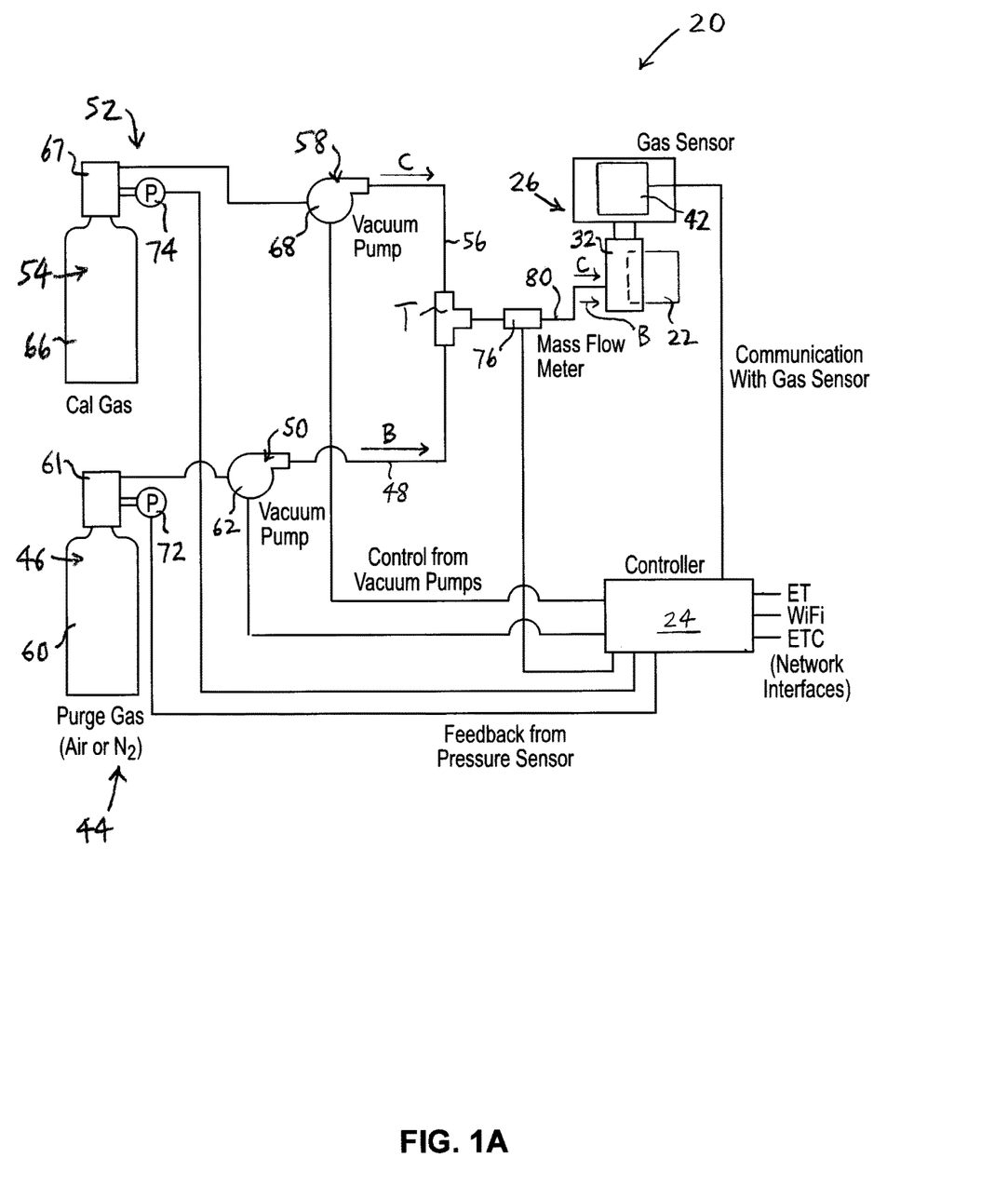
FIG. 1A is a schematic diagram of an embodiment of a system of the invention.

The direction of flow of the purge gas from the source 46 toward the fitting 36 is indicated by arrows "B" in FIG. 1A.

It will be understood that, as the purge gas is allowed to flow into the cavity 32 from the source 46 of the purge gas, the purge gas displaces such preselected gas as may have been present in the cavity 32. The purge gas may be any suitable gas, or mixture of gases. For example, the purge gas may be nitrogen ($N_2$), or air. It will also be understood that the displacement of the preselected gas by the purge gas would, in most circumstances, proceed over a relatively short period of time, until all of the preselected gas has been displaced, or alternatively, until the amount of the preselected gas that is present in the cavity is constant, i.e., not decreasing further.

Accordingly, the central controller 24 is configured so that, upon the sensor data indicating that the amount of the preselected gas in the cavity 32 has not changed over a preselected time period after the purge gas began flowing into the cavity 32, the central controller 24 de-activates the purge gas flow controller 50, to prevent the purge gas from flowing into the cavity 32. Upon the purge gas flow controller 50 being de-activated, final sensor data is generated by the sensor 22, the final sensor data indicating a final amount of the preselected gas that is detected by the sensor 22 as being present in the cavity 32 when the purge gas flow controller is de-activated.

If the final amount of the preselected gas that is indicated in the final sensor data is not greater than a predetermined maximum error threshold relative to zero, then the sensor 22 is not adjusted, i.e., the sensor 22 is acceptably close to zero. It will be understood that the maximum error threshold is a maximum acceptable error.

If the final amount of the preselected gas that is indicated in the final sensor data is greater than the predetermined maximum error threshold relative to zero, then the sensor 22 is adjusted so that the final amount of the preselected gas is read by the sensor 22 as zero. This is referred to as "zeroing" the sensor 22. Preferably, the adjustment of the sensor 22 is effected via the central controller 24.

After the sensor 22 is zeroed, it is checked to determine whether the adjusted sensor 22 accurately reads the final amount of the preselected gas as zero. If at that point the adjusted sensor 22 does not read the final amount as zero, then the sensor may have to be replaced, and a message in that regard is generated by the central controller 24, indicating that the sensor requires service.

The central controller 24 may be any suitable processor and/or controller. For example, in one embodiment, the central controller 24 may be a programmable logic controller. The central controller 24 preferably is connected with any suitable network or networks, via any suitable network interfaces (e.g., ET, WIFI, ETC).

From the foregoing, it can be seen that the system 20 is, advantageously, controlled by the central controller 24, which is controllable remotely. Those skilled in the art would appreciate that this enables the technician (not shown) to conduct testing (i.e., "zeroing") remotely from the sensor 22. In addition, the testing may be conducted by the technician "manually", i.e., initiated by the technician issuing suitable instructions to the central controller 24, or automatically, e.g., initiated by suitable instructions transmitted to the central controller 24 from another computer according to a predetermined schedule.

Those skilled in the art would appreciate that this enables the technician to conduct testing more efficiently, because the technician is not required to attend in person at the sensor to test it. Also, as noted above, the testing may be done automatically, which means that the technician may spend time only on reviewing the results of the testing.

The preselected gas may be, e.g., carbon monoxide (CO), or any other gas or mixture of gases that may be harmful, depending on the concentrations thereof.

In summary, testing or "zeroing" the sensor 22 involves allowing the purge gas (e.g., a suitable gas, such as nitrogen, or a suitable mixture of gases, such as air) to flow into the cavity 32, measuring the response of the sensor 22, and determining whether the response is acceptably close to zero. If the response is not acceptably close to zero, then the sensor 22 is adjusted, or "zeroed".

As is known in the art, it is necessary to test or "zero" the sensor 22 from time to time because sensors and their response characteristics change over time, necessitating re-zeroing.

Those skilled in the art would be aware of typical predetermined maximum error thresholds.

The system 20 preferably is also used for calibration. In one embodiment, the system preferably also includes a calibration assembly 52. Preferably, the calibration assembly 52 includes a source 54 of a calibration gas mixture (not shown). The calibration gas mixture includes the preselected gas in a known concentration, as will be described. The calibration assembly 52 preferably also includes calibration gas piping 56, for directing the calibration gas mixture from the source 54 of the calibration gas mixture to the cavity 32 of the housing body 30, via the fitting 36.

The known concentration of the preselected gas in the calibration gas mixture may be any suitable concentration. Those skilled in the art would be aware of suitable known concentrations. For example, if the preselected gas is carbon monoxide, then the known concentration may be 100 ppm.

It is also preferred that the calibration assembly 52 includes a calibration gas flow controller 58, for allowing the calibration gas mixture to flow along the calibration gas piping 56 from the source 54 of the calibration gas to the cavity 32 at a predetermined calibration gas flow rate.

Preferably, the central controller 24 is configured to activate the calibration gas flow controller 58, to cause the calibration gas mixture to flow through the calibration gas piping 56, and to de-activate the calibration gas flow controller 58, to prevent the calibration gas mixture from flowing through the calibration gas piping 56 to the cavity 32.

Upon the calibration gas flow controller 58 being activated, the calibration gas flow controller 58 allows the calibration gas mixture to flow into the cavity 32 at the predetermined calibration gas flow rate, and the sensor 22 detects the preselected gas in the cavity 32. The sensor 22 thereupon generates the sensor data that is transmitted to the central controller 24 at predetermined intervals. As noted above, the predetermined intervals may be any suitable intervals, e.g., approximately 0.50 seconds, or slightly less.

The direction of flow of the calibration gas mixture from the source 54 toward the fitting 36 is indicated by arrows "C" in FIG. 1A.

The central controller 24 is configured such that, upon the sensor data indicating that the amount of the preselected gas in the cavity 32 has not changed over a preselected time period, the central controller 24 de-activates the calibration gas flow controller, and final sensor data is generated. The final sensor data indicates a final amount of the preselected gas that is detected by the sensor 22 as being present in the cavity 32 when the calibration gas flow controller 58 is de-activated.

If the final amount of the preselected gas that is indicated in the final sensor data is not greater than a predetermined maximum error threshold relative to the known concentration of the preselected gas, then the sensor 22 is not adjusted. However, if the final amount of the preselected gas that is indicated in the final sensor data is greater than the predetermined maximum error threshold, then the sensor 22 is adjusted such that the final amount of the preselected gas is read by the sensor 22 as the known concentration. This may be referred to as "spanning". The adjustment may be made pursuant to instructions transmitted by the central controller.

After the sensor 22 is adjusted (i.e., spanned), it is checked to determine whether the adjusted sensor 22 accurately reads the final amount of the preselected gas as the known concentration. If at that point the adjusted sensor 22 does not read the final amount as the known concentration, then the sensor would have to be replaced, and a message in that regard is generated by the central controller 24, indicating that the sensor requires service.

In summary, calibrating or "spanning" the sensor 22 involves calibrating the sensor's response to the calibration gas mixture, to match the concentration of the calibration gas mixture (i.e., the concentration of the preselected gas in the calibration gas mixture). Calibrating, or spanning, involves allowing the calibration gas mixture to flow into the cavity 32, measuring the response of the sensor 22, and determining whether the response is acceptably close to the known concentration of the calibration gas mixture.

Calibration or "spanning" is necessary from time to time because sensors and their response characteristics change over time, necessitating periodic re-calibration.

As noted above, the system 20 is, advantageously, controlled by the central controller 24, which is controllable remotely. Those skilled in the art would appreciate that this enables the technician (not shown) to conduct calibration of the sensor 22 (i.e., "spanning") remotely from the sensor 22. In addition, the calibration may be conducted by the technician "manually", i.e., initiated by the technician issuing suitable instructions to the central controller 24, or automatically, e.g., initiated by suitable instructions transmitted to the central controller 24 from another computer according to a predetermined schedule.

Those skilled in the art would appreciate that this enables the technician to calibrate the sensor 22 more efficiently, because the technician is not required to attend in person at the sensor 22 for calibration. Also, as noted above, the calibration may be done automatically, which means that the technician may spend time only on reviewing the results of the calibration.

As can be seen in FIG. 6, the sensor control module 40 of the gas sensor assembly 26 preferably includes a module housing 38 in which the sensor unit processor 42 is located. Preferably, the module housing 38 and the housing body 30 are configured to fit together. Once they are secured to each other, as illustrated in FIG. 6, the sensor 22 and the sensor unit processor 42 are able to communicate with each other, via any suitable means. For example, there may be a hardwired connection between the sensor 22 and the sensor unit processor 42 to permit such communication, as schematically represented in FIG. 6 by dashed line 43. The local display, and connectivity interfaces (not shown) are located on the module housing 38 (FIG. 6). The probe assembly, or housing subassembly 28, may be a type of "smart sensor" recognized by the sensor unit processor 42 when the housing body 30 and the module housing 38 are connected together.

The direction of flow of the purge gas or the calibration gas mixture (as the case may be) into the cavity 32 via the fitting 35 is indicated in FIG. 6 by arrows "$D_1$", "$D_2$".

In normal operation of the gas sensor assembly 26, ambient atmospheric air diffuses through the filter 34, equilibrates in the cavity 32, and the sensor element 22 responds to the preselected gas (e.g., CO) that is present. It will be understood that the filter 34 is sufficiently permeable to allow ambient atmospheric gases to diffuse through the filter 34, while keeping out dust and other debris. The filter 34 may be any suitable filter. For example, the filter 34 may be a sintered metal type that is permeable to gas flow, with a pore size of approximately 100 microns. The direction of flow of the ambient atmosphere "A" into the cavity 32 (due to diffusion through the filter 34) is indicated in FIG. 6 by arrow "E".

During calibration/bump testing, the gas (i.e., the purge gas, or the calibration gas mixture, as the case may be) is provided through the fitting or inlet port 36 into the cavity at a nominal flow rate, e.g., approximately 0.5 liter per minute. The gas (the purge gas, or the calibration gas mixture) that is directed into the cavity 32 via the fitting or inlet port 36 flushes out the cavity 32 through the filter 34, into the ambient atmosphere. The direction of flow of the purge gas or the calibration gas mixture (as the case may be) from the cavity 32 through the filter 34 and into the ambient atmosphere "A" is indicated in FIG. 6 by arrow "F".

In calibration/testing operation, it is preferred that, when flushing out the cavity 32 with the gas (i.e., the purge gas or the calibration gas mixture, as the case may be), any pressure increase in the cavity 32 is minimal. This is because may types of sensors 22 (e.g., electrochemical sensors) are affected by pressure changes. Accordingly, the filter 34 preferably is sufficiently permeable that the filter 34 does not cause any appreciable pressure increase in the cavity 32 when the gas flowing into the cavity 32 via the fitting 36 is flowing at a rate of approximately 0.5 liter per minute.

Those skilled in the art would appreciate that the source of the purge gas 46 and the purge gas flow controller 50 may be provided in various forms, as will be described. For example, in one embodiment, the source 46 of the purge gas preferably is a purge gas reservoir (or cylinder) 60, and the source 46 of the purge gas preferably also includes a demand flow regulator 61 (FIG. 1A). The purge gas flow controller 50 may include a first vacuum pump or purge gas pump 62 (FIG. 1A), for pumping the purge gas along the purge gas piping 48 into the cavity 32. The purge gas pump 62 is activatable and de-activatable by the central controller 24. Those skilled in the art would appreciate that upon activation of the vacuum pump 62, the purge gas flows through the purge gas piping 48 to the cavity 32.

Figure 1B:
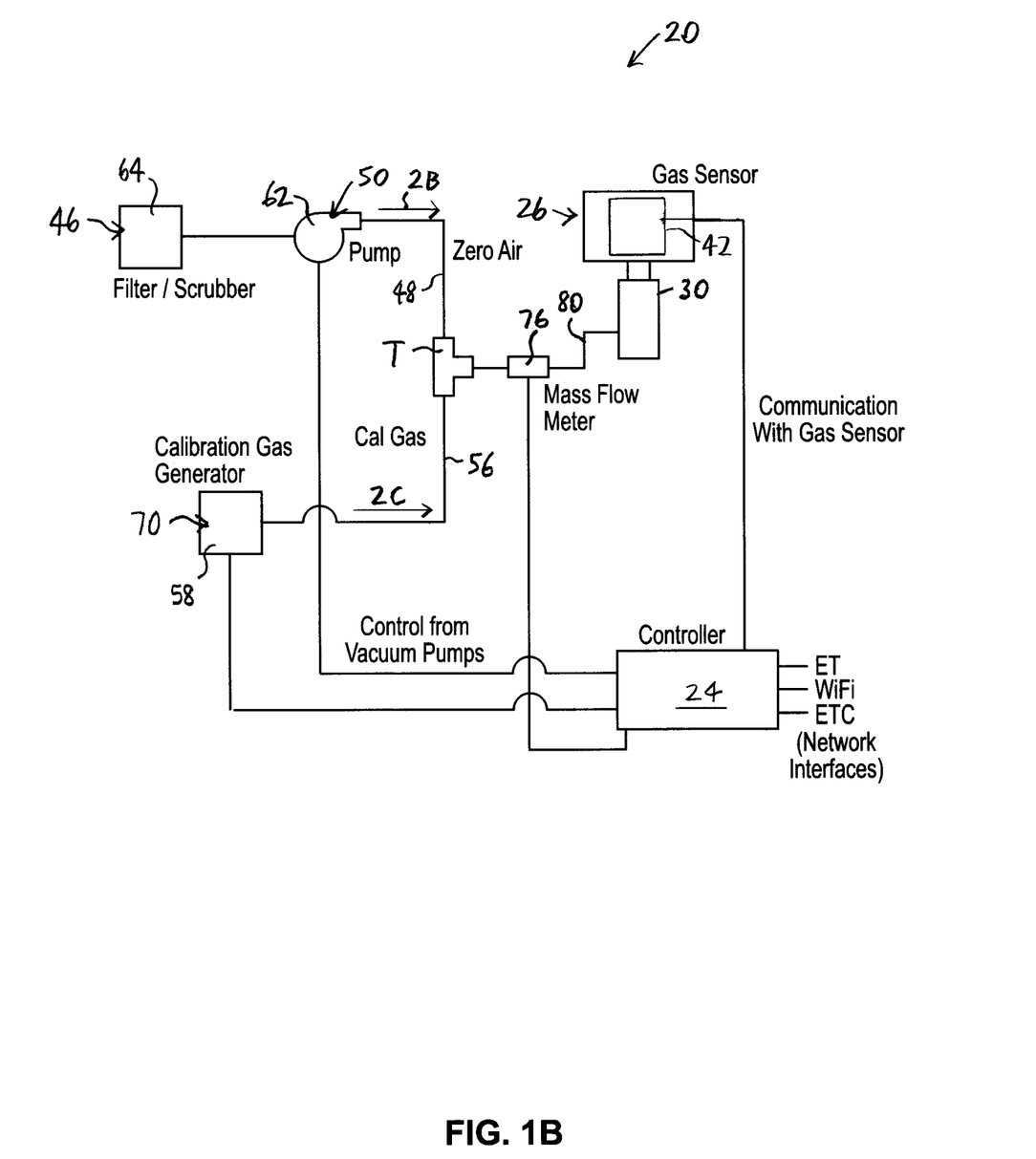
FIG. 1B is a schematic diagram of an alternative embodiment of the system of the invention.

The purge gas may be provided in any suitable manner. For example, in an alternative embodiment of the system 20, schematically illustrated in FIG. 1B, the source 46 of the purge gas preferably is an air pump/scrubber/filter subassembly 64. When activated, the purge gas pump 62 draws the purge gas from the air pump/scrubber/filter subassembly 64. The pump 62 preferably is activatable and de-activatable by the central controller 24. In FIG. 1B, the direction of flow of the purge gas from the air pump/scrubber/filter subassembly 64 toward the cavity 32 in the housing body 30 is indicated by arrow "2B".

Those skilled in the art would also appreciate that the source 54 of the calibration gas mixture and the calibration gas flow controller 58 may be provided in any suitable form. For example, in one embodiment, the source 54 of the calibration gas mixture preferably is a calibration gas reservoir (or cylinder) 66, and the source of the calibration gas mixture additionally includes a demand flow regulator 67 (FIG. 1A). The calibration gas flow controller 58 may include a second vacuum pump or calibration gas mixture pump 68, for pumping the calibration gas mixture along the calibration gas piping 56 into the cavity 32. The calibration gas mixture pump 68 preferably is activatable and de-activatable by the central controller 24. Those skilled in the art would appreciate that upon activation of the second vacuum pump 68, the calibration gas mixture flows through the calibration gas piping 56 to the cavity 32.

Each of the demand flow regulators 61, 67 (DFR) is normally in a shut (off) state, in which no gas is released to the output. Each DFR provides a positive gas shut-off, ensuring that no small leaks will drain gas, and empty the cylinder quickly. The cylinders containing the gas may be any suitable size.

The vacuum pumps 62, 68 are respectively connected to the DFRs 61, 67 via tubing or piping 48, 56 that may be any suitable tubing or piping. For example, the tubing 48, 56 may be any suitable plastic tubing. Preferably, when one of the pumps 62, 68 is switched on, a vacuum is produced, and this actuates the DFR to which the activated pump is connected, allowing the purge gas or the calibration gas mixture (as the case may be) to flow. The amount of vacuum required is any suitable amount. For example, the amount of vacuum may be approximately 3 inch WC, or less.

Accordingly, in this embodiment, each of the vacuum pumps 62, 68 preferably draws gas from the cylinder to which it is connected, at a controlled rate.

In operation, one of the two pumps 62, 68 can operate at any one time. Preferably, both the purge gas tubing 48 and the calibration gas tubing 56 lead to a tee "T", and an end section 80 of tubing brings the purge gas or the calibration gas mixture, as the case may be, from the tee "T" to the fitting or inlet port 36 (FIG. 1A). It will be understood that, for the purposes hereof, the end section 80 is considered to be included in the purge gas piping or tubing 48 when the purge gas is flowing to the cavity 32. Also, the end section 80 is considered to be included in the calibration gas mixture piping or tubing 56 when the calibration gas mixture is flowing to the cavity 32.

In the embodiment illustrated in FIG. 1B, the source 54 of the calibration gas mixture preferably is a calibration gas generator 70. Preferably, the calibration gas generator 70 includes the calibration gas flow controller 58. The direction of flow of the calibration gas mixture from the calibration gas generator 70 toward the cavity 32 in the housing body 30 is indicated by arrow "2C" in FIG. 1B.

In one embodiment, the system 20 additionally includes a purge gas pressure gauge 72 for determining a purge gas pressure of the purge gas in the source 46 of the purge gas (FIG. 1A).

In another embodiment, the system 20 preferably includes a calibration gas pressure gauge 74 for determining a calibration gas pressure of the calibration gas mixture in the calibration gas reservoir 66 (FIG. 1A).

It may be useful for an operator (not shown) to be able to confirm a mass of a gas flowing through the purge gas piping 48. Accordingly, in one embodiment, the system 20 preferably includes a mass flow meter 76 mounted in the purge gas piping 48, to measure a purge gas flow mass of the purge flow gas flowing through the purge gas piping 48. As can be seen in FIG. 1A, the mass flow meter 76 may be mounted in the end section 80 of the piping or tubing.

Similarly, it may be useful for the operator to be able to confirm an amount (i.e., a mass) of the calibration gas mixture that is flowing through the calibration gas piping 56. Preferably, the system 20 includes the mass flow meter 76 mounted in the calibration gas piping 56, to measure a calibration gas mixture flow mass of the calibration gas mixture flowing through the calibration gas piping 56. As noted above, in one embodiment, the mass flow meter 76 may be mounted in the end section 80, so that it can measure the mass of either the purge gas or the calibration gas mixture, depending on the gas that is flowing toward the cavity 32 in the housing body 30.

In one embodiment, the invention includes a method of testing the sensor 22. Preferably, the method includes, via the central controller 24, activating the purge gas flow controller 50, so that the purge gas flow controller 50 allows the purge gas to flow into the cavity 32 at the predetermined purge gas flow rate. As the purge gas flows into the cavity 32, the sensor 22 detects decreasing amounts of the preselected gas in the cavity 32. Once the sensor equilibrates (i.e., once the amount of the preselected gas is detected at zero, or almost zero, and is unchanging over time), the sensor 22 thereupon generates the sensor data that is transmitted to the central controller 24 at predetermined intervals.

Upon the sensor data indicating that the amount of the preselected gas in the cavity 32 has not changed over a preselected time period after the purge gas began flowing into the cavity 32, via the central controller 24, the purge gas flow controller 50 is de-activated. At that time, the final sensor data is generated by the sensor 22. The final sensor data indicates a final amount of the preselected gas that is detected by the sensor 22 as being present in the cavity 32 when the purge gas flow controller 50 is de-activated.

Preferably, if the final amount of the preselected gas that is indicated in the final sensor data is not greater than a predetermined maximum error threshold relative to zero, then the sensor 22 is not adjusted.

If the final amount of the preselected gas that is indicated in the final sensor data is greater than a predetermined maximum error threshold relative to zero, then, via the central controller 24, the sensor 22 is adjusted (i.e., "zeroed") so that the final amount of the preselected gas is read by the sensor 22 as zero. That is, if the final amount is greater than the predetermined maximum error threshold relative to zero, then the sensor 22 is "zeroed".

After the sensor 22 is zeroed, it is checked to determine whether the adjusted sensor 22 accurately reads the final amount of the preselected gas as zero. If at that point the adjusted sensor 22 does not read the final amount as zero, then the sensor may have to be replaced, and a message in that regard is generated by the central controller 24.

From the foregoing, it can be seen that the result of the method of testing the sensor 22 may that the sensor 22 is replaced. It will be understood that, if the sensor 22 is replaced, then the replacement sensor 22 is also tested, to ensure that it is accurate.

Once the sensor 22 (i.e., the sensor, or a replacement sensor, as the case may be) has been tested and found to be measuring the amount of the preselected gas within the predetermined maximum error threshold, it is preferred that the sensor 22 is subsequently calibrated. In one embodiment, the method of calibrating the sensor 22 preferably includes, via the central controller, activating the calibration gas flow controller 58. The calibration gas flow controller 58 allows the calibration gas mixture to flow into the cavity 32 at the predetermined calibration gas flow rate. As described above, the sensor 22 detects the preselected gas in the cavity 32. The sensor 22 thereupon generates the sensor data that is transmitted to the central controller 24 at predetermined intervals.

As noted above, the calibration gas mixture includes the preselected gas in a known concentration.

Accordingly, as the calibration gas mixture continues to flow into the cavity 32, the amount (i.e., concentration) of the preselected gas in the cavity 32 continues to change, until such concentration in the cavity 32 stabilizes, or equilibriates. The central controller 24 monitors the sensor data as the calibration gas mixture flows into the cavity 32. Preferably, the central controller 24 is configured to stop the calibration gas mixture from flowing into the cavity 32 once the amount (i.e., the concentration) of the preselected gas in the cavity 32 has stabilized.

Upon the sensor data indicating that the amount of the preselected gas in the cavity 32 (i.e., the concentration of the preselected gas in the cavity 32) has not changed over a preselected time period after the calibration gas mixture began flowing into the cavity (i.e., the calibration gas mixture is equilibriated), the flow of the calibration gas mixture into the cavity 32 is stopped. This is accomplished via the central controller 24 de-activating the calibration gas flow controller 58, which occurs when the central controller 24 determines that the concentration of the preselected gas in the cavity 32 has not changed over the preselected time period. Upon the central controller 24 de-activating the calibration gas flow controller 58, final sensor data is generated, the final sensor data indicating a final amount of the preselected gas that is detected by the sensor 22 as being present in the cavity 32, when the calibration gas flow controller 58 is de-activated.

From the foregoing, it can be seen that the final amount of the preselected gas in the cavity 32 is expected to be the same, or almost the same, as the known concentration of the preselected gas in the calibration gas mixture. If the final amount of the preselected gas that is indicated in the final sensor data is not greater than a predetermined maximum error threshold relative to the known concentration of the preselected gas, then sensor 22 is not adjusted.

If the final amount of the preselected gas that is indicated in the final sensor data is greater than the predetermined maximum error threshold relative to the known concentration of the preselected gas, then the sensor is adjusted, so that the final amount of the preselected gas is read by the sensor as the known concentration of the preselected gas. In effect, the sensor 22 is reset, to read the actual concentration in the cavity as the known concentration in the calibration gas mixture.

It will be understood that the maximum error threshold for the purge gas measurement and the maximum error threshold for the calibration gas mixture measurement may be different.

After the sensor 22 is adjusted or spanned, it is checked to determine whether the adjusted sensor 22 accurately reads the final amount of the preselected gas as the known concentration. If at that point the adjusted sensor 22 does not read the final amount as the known concentration, then the sensor may have to be replaced, and a message in that regard is generated by the central controller 24. If the sensor is replaced, then the replacement sensor also is tested, and calibrated after installation.

Figure 4:
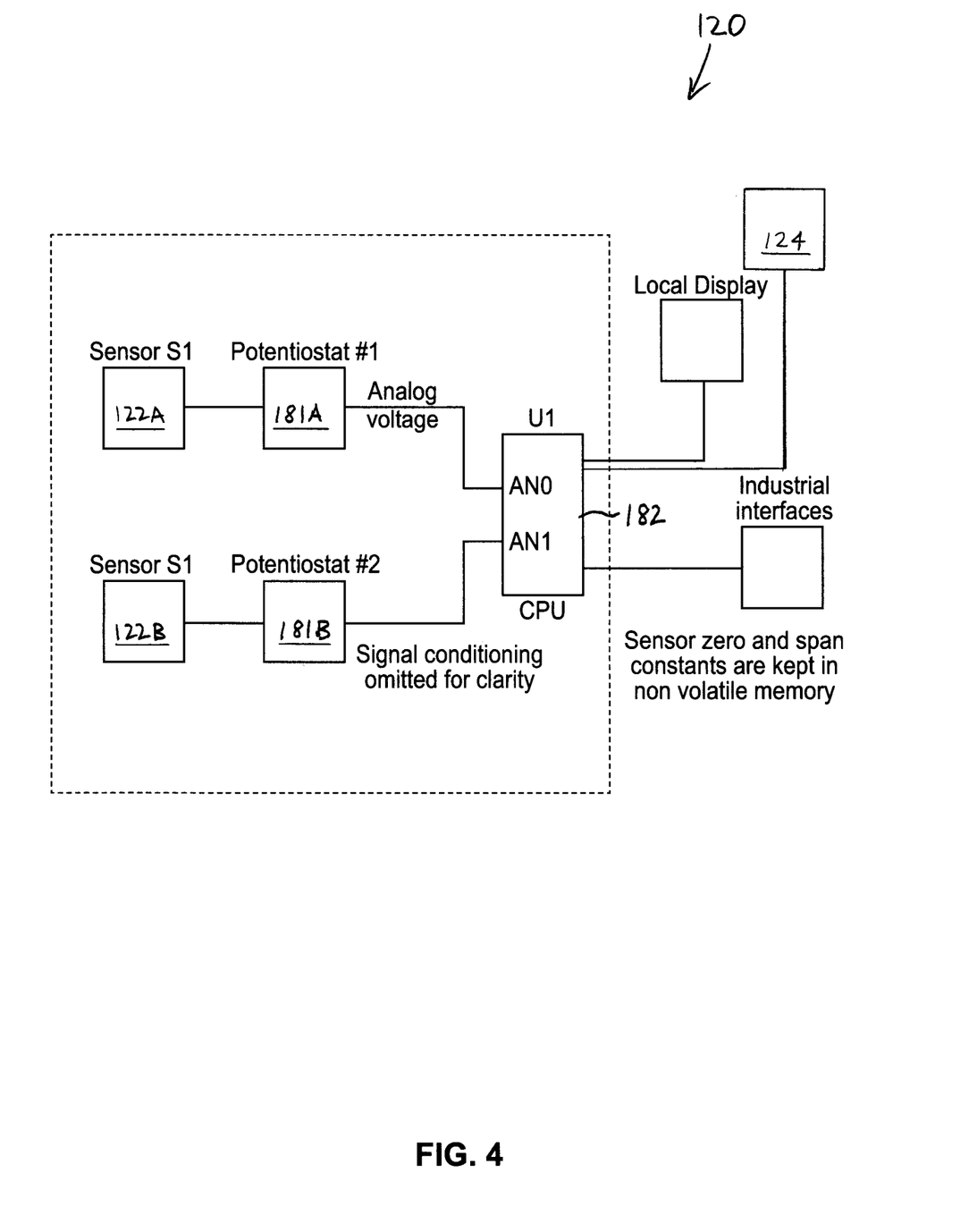
FIG. 4 is a schematic diagram of another alternative embodiment of the system of the invention.

Those skilled in the art would be aware that, in many industries, the gas sensors are required to be capable of non-stop performance, as well as accuracy. An alternative embodiment of the system 120 is schematically illustrated in FIG. 4. Preferably, the system 120 includes first and second gas sensors 122A, 122B. As will be described, the dual-sensor redundant topology is utilized because non-stop sensing performance is required. As will also be described, if one of the sensors fails, then the faulty sensor may be disabled, and the other (non-faulty) sensor may continue to function.

It will be understood that the sensors 122A, 122B are both in fluid communication with the same cavity in a housing body (not shown in FIG. 4). It is also preferred that the first and second sensors 122A, 122B are configured to produce respective first and second output currents upon sensing the preselected gas in the cavity.

Preferably, the system 120 also includes first and second potentiostats 181A, 181B, electrically connected to the first and second gas sensors 122A, 122B respectively, for converting said first and second output currents into corresponding first and second voltage outputs. In response to the preselected gas in the cavity, the sensors 122A, 122B produce respective current outputs that are applied to the respective inputs of potentiostats 181A, 181B.

The potentiostats 181A, 181B provide biasing for the sensors 122A, 122B, and include respective transimpedance amplifiers (not shown), converting the current signal from the sensors 122A, 122B into respective voltage outputs, which each may be converted into a digital signal by the A/D converter of a sensor unit processor 182 (e.g., a microprocessor).

Based on the first and second voltage outputs, the sensor unit processor 182 determines respective first and second concentrations of the preselected gas in the cavity 132.

Preferably, the sensor unit processor 182 is configured to compare the first and second concentrations, and to determine whether the first and second concentrations differ from each other by a difference amount that is greater than a predetermined acceptable difference amount. It will be understood that the difference amount is the difference between the concentrations of the preselected gas in the cavity 132 as determined by each of the sensors 122A, 122B respectively, once equilibriated.

It is preferred that the sensor unit processor 182 has multiple analog-to-digital converters, with adequate resolution (12 bits, for example). Preferably, the sensor unit processor or microprocessor 182 is in communication with a central controller 124, as will be described.

The sensors 122A, 122B preferably are of the same type, e.g., the sensors 122A, 122B may be electrochemical sensors, for sensing carbon monoxide.

It will also be understood that the system 120 preferably also includes other elements described above, so that the sensors 122A, 122B may be tested, at the same time, or at substantially the same time. Similarly, the system 120 may also include the additional elements described above, for calibrating the sensors 122A, 122B at the same time, or at substantially the same time.

The microprocessor 182 preferably applies a zero correction (baseline compensation) as well as span calibration, using constants that are determined during sensor zeroing and spanning. This allows the microprocessor 182 to calculate actual gas concentrations, usually in ppm, of the target (preselected) gas, e.g., carbon monoxide.

In operation, the microprocessor 182 may use the outputs of one of the sensors 122A, 122B, or the outputs of both sensor 122A, 122B, when both of the sensors 122A, 122B are operating normally. For example, if both of the sensors 122A, 122B are operating normally, then the microprocessor 182 may average the outputs of the sensors 122A, 122B.

In normal operation, gas concentrations are calculated for each of the sensors 122A, 122B, and are in close agreement with each other.

However, if the ppm readings from the sensors 122A, 122B differ from each other by a predetermined amount, then the central controller 24 initiates a calibration test to determine which of the sensors 122A, 122B has failed. Once that has been determined, the central controller 124 preferably disables the faulty one of the sensors 122A, 122B, and the central controller 124 logs the event.

It will be understood that various communication interfaces (e.g., local display and industrial interfaces) may also be in communication with the microprocessor 182 and/or the central controller 124 (FIG. 4).

From the foregoing, it can be seen that gas sensor assembly 26 preferably permits remote calibration and testing. Preferably, remote calibration and testing would effected be via a suite of commands to select calibration/test modes.

It is preferred that the gas sensor assembly 26 includes the following:
(i) means for outputting the response of the sensor 22 (digital or analog);
(ii) means to zero the sensor, by "save zero" command, preferably by digital means;
(iii) means to span the sensor, by "save span" command, preferably by digital means;
(iv) means to enter zero/span mode.

It is also preferred that the gas sensor assembly 26 provides the following commands:
(i) exit to "run mode" (i.e., run normally);
(ii) exit zero mode;
(iii) exit span mode;
(iv) exit to run mode.

Other preferred features of the gas sensor assembly 26 include the fitting 36, via which the calibration gas mixture and the purge gas may flow into the cavity 32, so that the calibration gas mixture and the purge gas in the cavity are in fluid communication with the sensor 22. Also, when the calibration gas mixture or the purge gas is not being introduced into the cavity, the sensor 22 is exposed to ambient atmospheric air, usually through the filter 34 (preferably, a permeable sintered filter) to keep out dust.

Manual Operation Calibration and Testing Example

Figure 2:
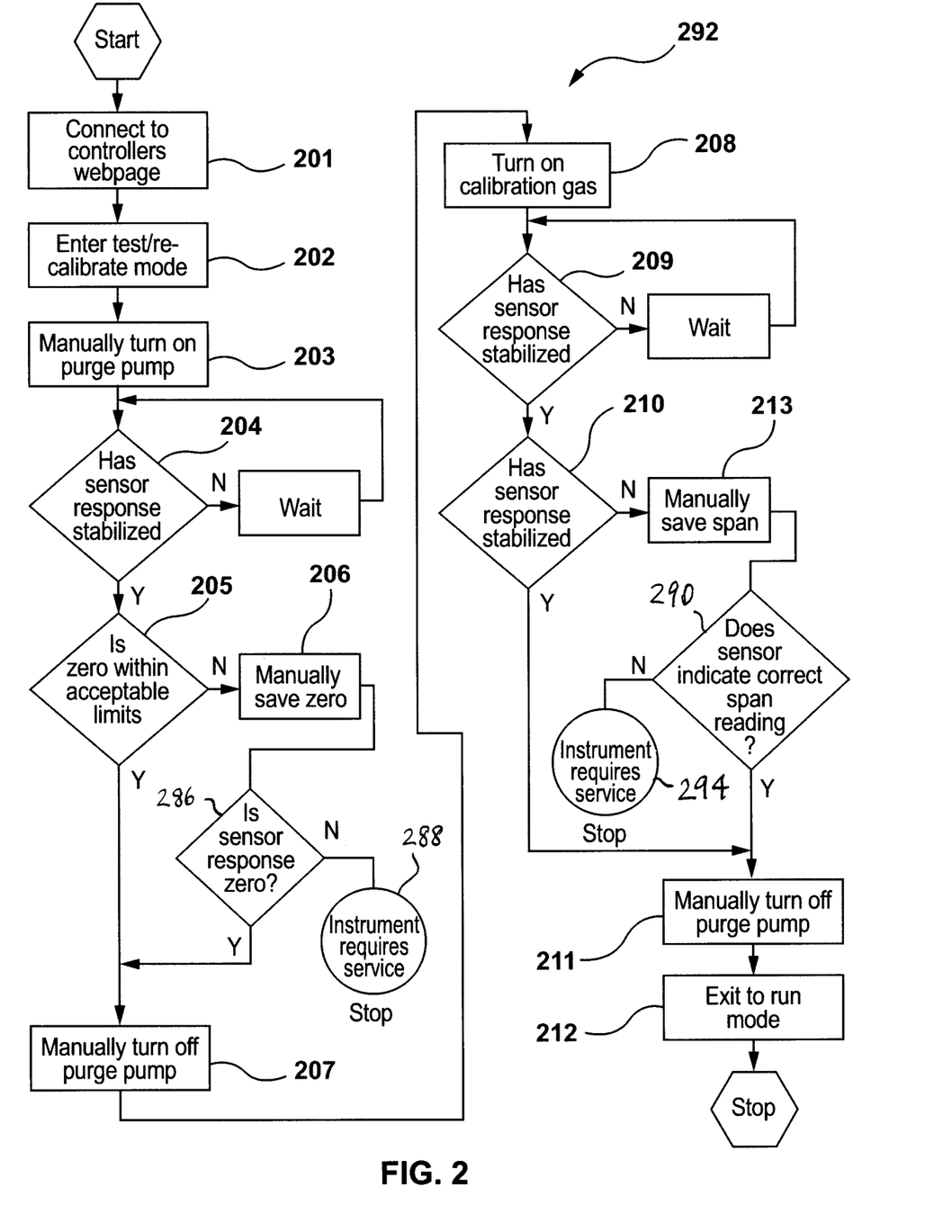
FIG. 2 is a flow chart schematically illustrating an embodiment of a method of the invention.

In this operational mode, schematically illustrated in FIG. 2, via a computer over a network, the technician connects to the central controller 24 for a mode identified as Gas Sensor Under Test. It is preferred that a web server approach is utilized, so that the technician can use a regular desktop computer or smart phone or other internet-connected device to do this work.

Preferably, in this mode, the central controller 24 operates as a web-page server, and the technician can manually carry out the steps to bump test, test zero, zero, span, enter normal run mode, as well as to configure the gas sensor 22 that is under test.

In one embodiment, the procedure may involve the following steps, as shown in FIG. 2:

Step 201: connect to the central controller 24 and view the web server page;

Step 202: enter calibration/test mode;

Step 203: commence Zero Test: activate the first vacuum pump 62 for the purge gas;

Step 204: observe the response of the sensor 22 to the purge gas;

the sensor 22 responds to the purge gas in the cavity 32, and equilibrium is reached;

Step 205: if, after equilibrium is reached, the sensor response is acceptably close to zero, the purge gas vacuum pump 62 is de-activated, and the procedure proceeds to step 292, bump test/recalibration;

Step 206: if, after equilibrium is reached, the sensor response is not acceptably close to zero, the technician can, using a button on the web server page, issue a command "save zero", that establishes the new updated zero, for the sensor;

Step 286: the zeroed sensor may be tested, to determine whether the sensor indicates that there is zero preselected gas in the cavity;

Step 207: If the zeroed sensor responds by indicating that there is zero preselected gas in the cavity, the technician de-activates the purge gas vacuum pump 62;

Step 288: if the zeroed sensor does not properly read the amount of the preselected gas in the cavity as zero, then the instrument requires service (e.g., replacement), and a message in that regard is transmitted;

Step 292: bump test/recalibration:

Step 208: the technician, using a command from the web server page, activates the second vacuum pump 68;

Step 209: observe the response of the sensor to the calibration gas mixture. The sensor responds to the calibration gas mixture, and the technician observes the response of the sensor 22 to the calibration gas mixture;

Step 210: if, after equilibrium is reached, the sensor response is acceptably close to what it should be;

Step 211: the technician de-activates the calibration gas vacuum pump 68;

Step 212: the technician may then, using a command on the web server page, cause the gas sensor to exit calibration/test mode, and enter normal run mode;

Step 213: if, after equilibrium is reached, the sensor response is not acceptably close to the known concentration, the technician, using the "save span" command on the web page, can recalibrate the sensor's response to the calibration gas;

Step 290: the adjusted ("spanned") sensor may be tested, to determine whether the sensor indicates that there is the known concentration of preselected gas in the cavity;

When the response is within acceptable limits (FIG. 2):

Step 211: the technician de-activates the calibration gas vacuum pump 68;

Step 212: the technician may then, using a command on the web server page, cause the gas sensor to exit calibration/test mode, and enter normal run mode.

Figure 7:
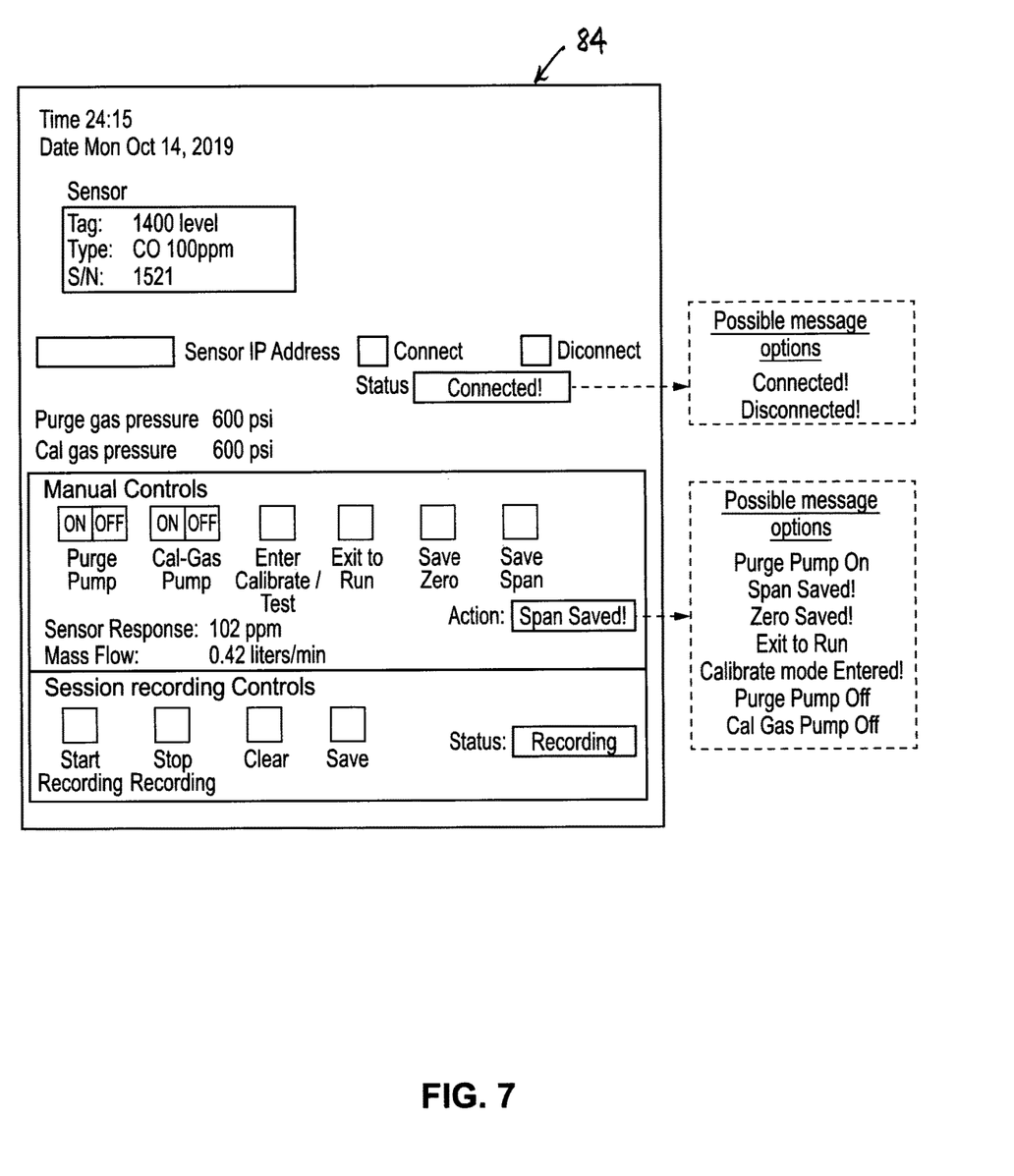
FIG. 7 is an example of a webserver screen for manual remote calibration/testing in accordance with the invention.

Step 294: If the adjusted sensor does not properly indicate that there is the known concentration of the preselected gas in the cavity, then the instrument requires service (e.g., replacement), and a message in that regard is transmitted An example of a webserver screen 84, for manual remote calibration/testing, is shown in FIG. 7. In one embodiment, this is preferably served by the central controller 24 over an Ethernet network. The information provided in the example gives the technician a total "situational awareness", even though the technician is working remotely from the sensor 22. From the foregoing, it can be seen that every aspect of the manual calibration/testing of the gas sensor 22 is under the technician's control.

Figure 5A:
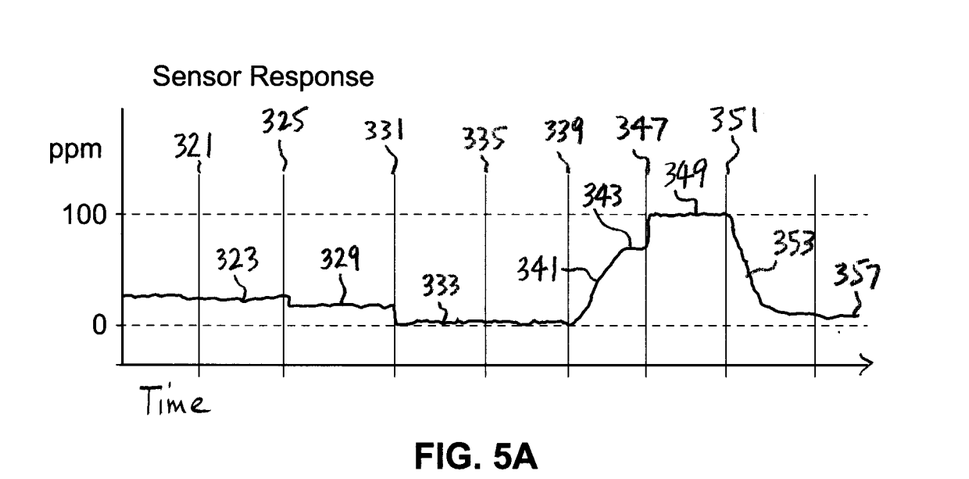
FIG. 5A is an example of a manual calibration/test session recording of a sensor response.
Figure 5B:
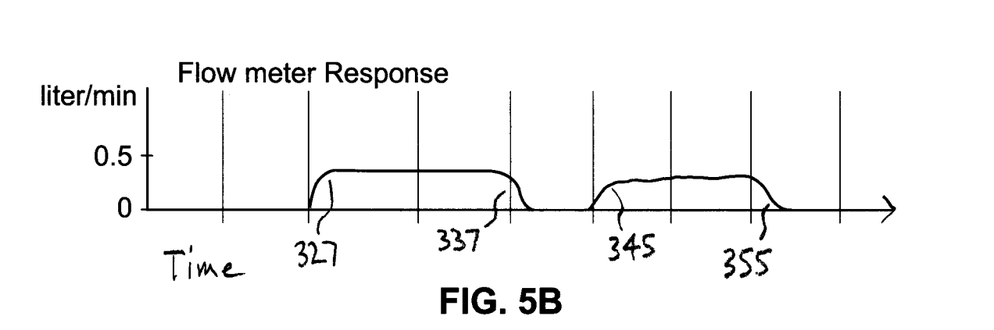
FIG. 5B is an example of a manual calibration/test session recording of a flow meter response.

FIGS. 5A and 5B show an example of a manual calibration/test session recording, starting with an unzeroed/incorrectly spanned gas sensor 22, and ending with a zeroed/correctly spanned gas sensor 22. It will be understood that FIGS. 5A and 5B are vertically aligned, to show the sensor response and the flow meter response at corresponding times.

The horizontal axis in each of FIGS. 5A and 5B is time. However, it will also be understood that the vertical lines in FIGS. 5A and 5B do not necessarily represent equal time intervals. Instead, the vertical lines are intended to indicate events and responses, for example, reference character 325 indicates the point at which the first vacuum pump 62 is activated, and reference character 327 indicates the point at which the mass flow indicator 76 responds to the flow of the purge gas through the mass flow indicator 76.

Such a session recording is very useful for field calibration/testing reports.

The steps illustrated in FIGS. 5A and 5B are as follows.

Step 321: entry of test/calibration mode;

Step 323: Sensor 22 response to ambient air;

Step 325: Zero gas pump (first vacuum pump 62) activated;

Step 327: mass flow indicator 76 responds;

Step 329: Sensor 22 is not zeroed, with zero gas applied;

Step 331: Zero is saved;

Step 333: Sensor 22 is correctly zeroed, with zero gas still on;

Step 335: De-activate first (purge gas) vacuum pump 62;

Step 337: Mass flow indicator 76 responds;

Step 339: Second vacuum pump 68 activated, to pump the calibration gas mixture;

Step 341: Sensor 22 responds to 100 ppm calibration gas mixture;

Step 343: Steady state response (equilibrium) to the calibration gas mixture, sensor 22 is not correctly spanned;

Step 345: Mass flow indicator 78 responds to calibration gas mixture flow;

Step 347: Span is saved;

Step 349: Sensor 22 now reads the correct concentration of the calibration gas mixture;

Step 351: Second vacuum pump 68 de-activated;

Step 353: Sensor response after flow of calibration gas mixture stopped;

Step 355: Mass flow indicator 78 responds to flow of calibration gas mixture ending;

Step 357: Sensor responding accurately to the preselected (target) gas (CO) in the ambient air.

Automatic Calibration and Testing Example

Figure 3:
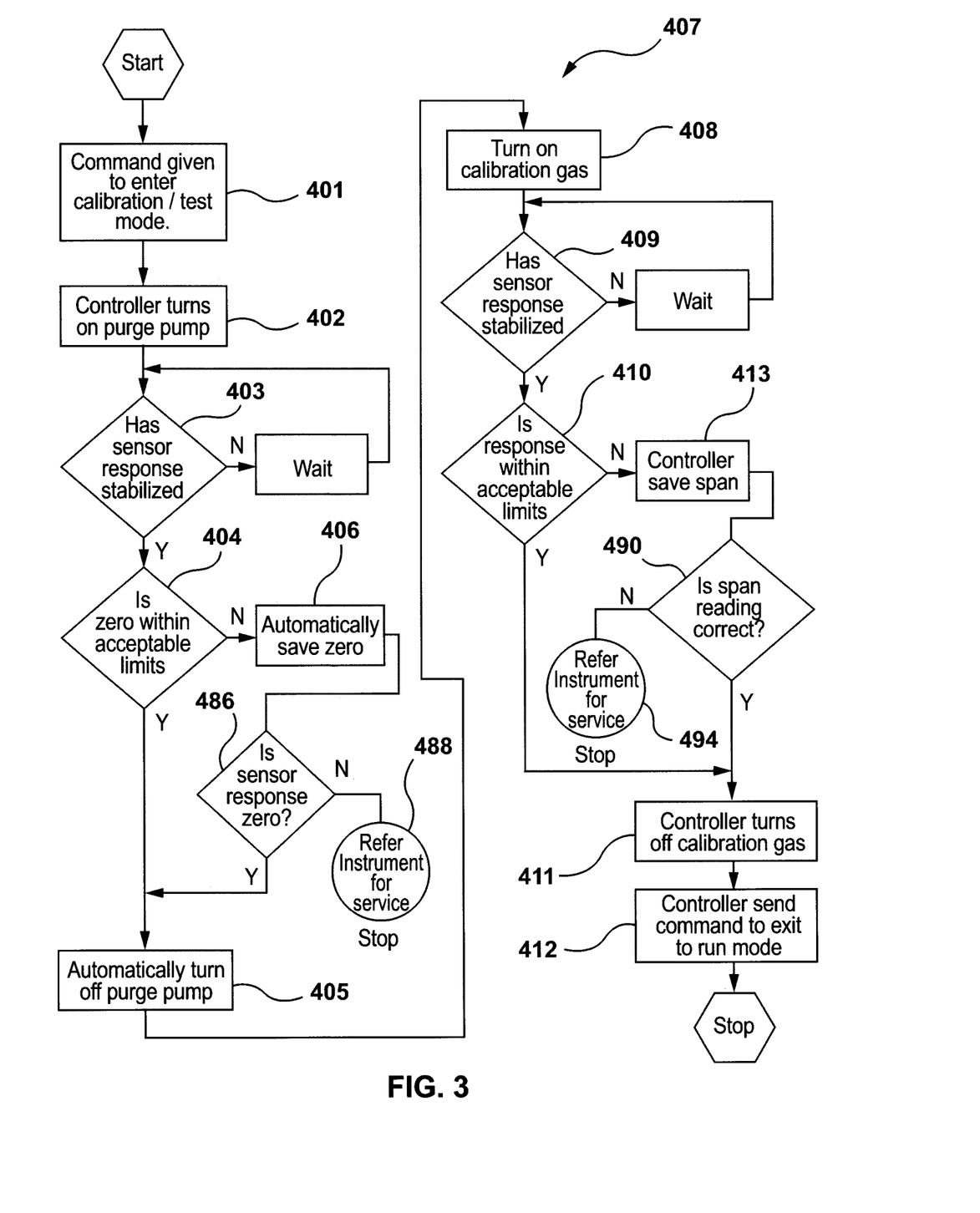
FIG. 3 is a flow chart schematically illustrating an alternative embodiment of the method of the invention.

In one embodiment, schematically illustrated in FIG. 3, the entire sequence described is carried out by the central controller 24, once the central controller 24 is given the test/re-calibration command or test command (no recalibration or re-zero).

Preferably, a command is sent to the central controller 24, using a network connection, to enter the test or test/recalibration mode. The originator of the command may be a SCADA system.

Referring to FIG. 3, the steps are as follows:

Step 401: enter calibration/test mode by issuing a command to central controller 24 over the network;

Step 402: Zero Test: the controller 24 turns on the vacuum pump 62 for the purge gas;

Step 403: the sensor 22 responds to the purge gas, time is allowed for a steady state (equilibrium) response to be reached.

Once the sensor response stabilizes:

Step 404: if, after equilibrium is reached, the sensor response is acceptably close to zero, the Zero test is passed;

Step 405: the purge gas vacuum pump 62 is turned off automatically and proceed to step 408, bump test/recalibration;

Step 406: if, after equilibrium is reached, the sensor response is not acceptably close to zero, a "save zero" command is given automatically, that establishes the new updated zero, for the sensor 22 (i.e., the sensor is zeroed);

Step 486: the zeroed sensor may be tested, to determine whether the sensor indicates that there is zero preselected gas in the cavity;

Step 405: if the zeroed sensor functions properly, the purge gas vacuum pump 62 is automatically switched off;

Step 488: if the zeroed sensor does not properly read the amount of the preselected gas in the cavity as zero, then the instrument requires service (e.g., replacement), and a message in that regard is transmitted;

Step 407: bump test/recalibration:

Step 408: the central controller 24 turns on the calibration gas vacuum pump 68; Step 409: the sensor 22 responds to the calibration gas, and reading stabilizes; Step 410: if, after equilibrium is reached, the sensor response is acceptably close to what it should be, then the calibration test is passed;

The calibration test is passed;

Step 411: the controller 24 turns off the calibration gas vacuum pump 68;

Step 412: the controller 24 sends a command to cause the gas sensor assembly 26 to exit calibration/test mode, and enter normal run mode (i.e., the old span is still acceptable);

Step 413: if, after equilibrium is reached, the sensor response is not acceptably close to what it should be, the controller, using the "save span" command, recalibrates the sensor's response to the calibration gas;

Step 490: the adjusted ("spanned") sensor may be tested, to determine whether the sensor indicates that there is the known concentration of preselected gas in the cavity;

Once the response is within acceptable limits (FIG. 3):

Step 411: the controller 24 turns off the calibration gas vacuum pump 68;

Step 412: the controller 24 sends a command to cause the gas sensor assembly 26 to exit calibration/test mode, and enter normal run mode.

Step 494: If the adjusted sensor does not properly indicate that the known concentration of the preselected gas is in the cavity, then the instrument requires service (e.g., replacement), and a message in that regard is transmitted Although examples are given and discussed for a sensor that can detect only one gas for simplicity (FIG. 1A), it will be apparent to those skilled in the art that the embodiment of the system 20 schematically illustrated in FIG. 1A may be easily modified to provide manual/automatic testing/calibration sensors that detect more than one gas (multigas detection). For example, a third cylinder of calibration gas with an associated vacuum pump may be added, in various arrangements to accommodate multi-gas sensors.

It will be appreciated by those skilled in the art that the invention can take many forms, and that such forms are within the scope of the invention as claimed. The scope of the claims should not be limited by the preferred embodiments set forth in the examples, but should be given the broadest interpretation consistent with the description as a whole.

We claim:

1. A method comprising:
   (a) providing a central controller;
   (b) providing at least one gas sensor assembly, comprising:
      a housing subassembly comprising:
         a housing body defining a cavity therein in fluid communication with an ambient atmosphere;
         a filter between the cavity and the ambient atmosphere permitting fluid communication therethrough;
         a fitting, through which a gas is flowable into the cavity;
         first and second gas sensors in fluid communication with the cavity, said first and second gas sensors being configured to detect amounts of at least one preselected gas that is located in the cavity, said first and second gas sensors being configured to generate first and second sensor data respectively including first and second detected amounts of said at least one preselected gas that are detected by the first and second gas sensors;
      a sensor control module, comprising:
         a sensor unit processor, for receiving incoming signals from the central controller, and for transmitting outgoing signals to the central controller;
         the sensor unit processor being configured to receive the first and second sensor data and to transmit the first and second sensor data in outgoing signals to the central controller;
   (c) providing a test assembly, comprising:
      a source of a purge gas;
      purge gas piping, for directing the purge gas from the source of the purge gas to the cavity of the housing via the fitting;
      a purge gas flow controller, for allowing the purge gas to flow along the purge gas piping from the source of the purge gas to the cavity at a predetermined purge gas flow rate;
   (d) with the central controller, activating the purge gas flow controller, to cause the purge gas flow controller to allow the purge gas to flow into the cavity at the predetermined purge gas flow rate, to at least partially displace said at least one preselected gas from the cavity;
   (e) while the purge gas flows into the cavity, with said first and second gas sensors, generating the first and second sensor data that is transmitted to the central controller at predetermined time intervals;
   (f) with the central controller, upon the first and second sensor data indicating that the first and second detected amounts of said at least one preselected gas in the cavity have not changed over a preselected time period after the purge gas began flowing into the cavity, de-activating the purge gas flow controller, to stop the purge gas flowing into the cavity;
   (g) with the first and second gas sensors, detecting final first and second detected amounts of said at least one preselected gas in the cavity;
   (h) comparing the final first and second detected amounts of said at least one preselected gas to zero, wherein when said final first and second detected amounts do not respectively differ from zero by more than a predetermined maximum error threshold, then said first and second gas sensors are not adjusted;
   (i) when an incorrect one of said final first and second detected amounts, detected by an identified one of the first and second gas sensors, differs from zero by an error that is more than the predetermined maximum error threshold, then the identified one of said first and second gas sensors is adjusted to correct the error, to provide an adjusted identified one of the first and second gas sensors;
   (j) with the adjusted identified one of said first and second gas sensors, detecting a test detected amount of said at least one preselected gas is in the cavity; and
   (k) when the test detected amount differs from zero by more than the predetermined maximum error threshold, disabling the adjusted identified one of the first and second gas sensors.

2. The method according to claim 1, additionally comprising:
   (l) replacing the disabled adjusted identified one of the first and second gas sensors with a replacement gas sensor.

3. A method comprising:
   (a) providing a central controller;
   (b) providing at least one gas sensor assembly, comprising:
      a housing subassembly comprising:
         a housing body defining a cavity therein in fluid communication with an ambient atmosphere;
         a filter between the cavity and the ambient atmosphere permitting fluid communication therethrough;
         a fitting, through which a gas is flowable into the cavity;
         first and second gas sensors in fluid communication with the cavity, said first and second gas sensors being configured to detect amounts of at least one preselected gas that is located in the cavity, said first and second gas sensors being configured to generate first and second sensor data respectively including first and second detected amounts of said at least one preselected gas that are detected by the first and second gas sensors;

a sensor control module, comprising:

a sensor unit processor, for receiving incoming signals from the central controller, and for transmitting outgoing signals to the central controller;

the sensor unit processor being configured to receive the first and second sensor data and to transmit the first and second sensor data in outgoing signals to the central controller;

(c) providing a calibration assembly, the calibration assembly comprising:

a source of a calibration gas mixture, the calibration gas mixture comprising said at least one preselected gas in a known concentration;

calibration gas piping, for directing the calibration gas mixture from the source of the calibration gas mixture to the cavity of the housing, via the fitting;

a calibration gas flow controller, for allowing the calibration gas mixture to flow along the calibration gas piping from the source of the calibration gas mixture to the cavity at a predetermined calibration gas flow rate;

(d) the central controller, activating the calibration gas flow controller, to cause the calibration gas flow controller to allow the calibration gas mixture to flow into the cavity at the predetermined calibration gas flow rate;

(e) while the calibration gas mixture flows into the cavity, with said first and second gas sensors, generating the first and second sensor data that is transmitted to the central controller at predetermined time intervals;

(f) with the central controller upon the first and second sensor data indicating that the first and second detected amounts of said at least one preselected gas in the cavity have not changed over a preselected time period after the calibration gas mixture began flowing into the cavity, de-activating the calibration gas flow controller, to stop the calibration gas mixture flowing into the cavity;

(g) with the first and second gas sensors, detecting final first and second detected amounts of said at least one preselected gas in the cavity;

(h) comparing the final first and second detected amounts of said at least one preselected gas to the known concentration thereof, wherein when the final first and second detected amounts do not respectively differ from the known concentration by more than a predetermined maximum error threshold, then the first and second gas sensors are not adjusted;

(i) when an incorrect one of said final first and second detected amounts, detected by an identified one of the first and second gas sensors, differs from the known concentration by an error that is more than the predetermined maximum error threshold, then the identified one of the first and second gas sensors is adjusted to correct the error, to provide an adjusted identified one of the first and second gas sensors;

(j) with the adjusted identified one of said first and second gas sensors, detecting a test detected amount of said at least one preselected gas in the cavity; and (k) when the test detected amount differs from the known concentration of said at least one preselected gas by more than the predetermined maximum error threshold, disabling the adjusted identified one of the first and second gas sensors.

4. The method according to claim 3, additionally comprising:

(l) replacing the disabled adjusted identified one of the first and second gas sensors with a replacement gas sensor.

* * * * *